(12) United States Patent
Densham (10) Patent No.: US 7,008,766 B1
(45) Date of Patent: *Mar. 7, 2006

(54) NUCLEIC ACID SEQUENCE ANALYSIS (75) Inventor: Daniel Henry Densham, Devon (GB)

(73) Assignee: Medical Biosystems, Ltd. (GB)

( * ) Notice: Subject to any disclaimer, the term of this patent is extended or adjusted under 35 U.S.C. 154(b) by 15 days.

This patent is subject to a terminal disclaimer.

(21) Appl. No.: 09/463,549

(22) PCT Filed: Jul. 24, 1998

(86) PCT No.: PCT/GB98/02214

§ 371 (c)(1),
(2), (4) Date: Jan. 27, 2000

(87) PCT Pub. No.: WO99/05315

PCT Pub. Date: Feb. 4, 1999

(30) Foreign Application Priority Data

Jul. 28, 1997 (GB) ............................................. 9715942
Dec. 22, 1997 (GB) ............................................. 9727103

(51) Int. Cl.
C12Q 1/68 (2006.01)
C12P 19/34 (2006.01)
C07H 21/02 (2006.01)

(52) U.S. Cl. .......................... 435/6; 435/91.1; 435/183; 536/23.1; 536/24.31; 536/24.33

(58) Field of Classification Search ..................... 435/6, 435/91.1, 91.2, 183, 287.2; 436/800, 805, 436/94, 518; 536/23.1, 24.31, 24.33, 24.3, 536/24.32, 26.6; 935/6
See application file for complete search history.

(56) References Cited

U.S. PATENT DOCUMENTS

| 4,971,903 | A |   | 11/1990 | Hyman |
| 5,360,714 | A | * | 11/1994 | Seeger |
| 5,485,277 | A | * | 1/1996  | Foster ........................ 356/445 |
| 5,620,854 | A |   | 4/1997  | Holzrichter et al. ........... 438/6 |
| 5,753,439 | A | * | 5/1998  | Smith et al. .................... 435/6 |
| 5,801,042 | A | * | 9/1998  | Chang et al. ............. 435/252.3 |
| 6,159,687 | A | * | 12/2000 | Vind .............................. 435/6 |
| 6,221,642 | B1 | * | 4/2001  | O'Donnell .................. 435/194 |
| 6,331,392 | B1 |   | 12/2001 | Laing et al. |
| 6,623,929 | B1 | * | 9/2003  | Densham ....................... 435/6 |

FOREIGN PATENT DOCUMENTS

| EP | 0 223 618 A2 | 5/1987 |
| EP | 0 425 563 B1 | 5/1991 |
| WO | 9005303      | 5/1990 |
| WO | 9013666      | 11/1990 |
| WO | 9106678      | 5/1991 |
| WO | 9321340      | 10/1993 |
| WO | 9421822      | 9/1994 |
| WO | WO 95/06138 A1 | 3/1995 |

OTHER PUBLICATIONS

Schwarz, T. (1991) "Detection of Nucleic Acid Hybridization Using Surface Plasmon Resonance" *Trends in Biotechnology* 9(10):339–340.

* cited by examiner

Primary Examiner—Bradley L. Sisson
(74) Attorney, Agent, or Firm—Saliwanchik, Lloyd & Saliwanchik (57) ABSTRACT The present invention relates to a method for determining the sequence of a polynucleotide, the method comprising the steps of: (i) reacting a target polynucleotide with a polymerase enzyme immobilised on a solid support, and the different nucleotides, under conditions sufficient for the polymerase reaction; and (ii) detecting the incorporation of a specific nucleotide complementary to the target polynucleotide, by measuring radiation.

24 Claims, 5 Drawing Sheets

NUCLEIC ACID SEQUENCE ANALYSIS

This application is the U.S. national stage application of International patent application No. PCT/GB98/02214, filed Jul. 24, 1998.

FIELD OF THE INVENTION

This invention relates to a method for determining the sequence of a polynucleotide.

BACKGROUND OF THE INVENTION

The ability to determine the sequence of a polynucleotide is of great scientific importance. For example, the Human Genome Project is an ambitious international effort to map and sequence the three billion bases of DNA encoded in the human genome. When complete, the resulting sequence database will be a tool of unparalleled power for biomedical research. The major obstacle to the successful completion of this project concerns the technology used in the sequencing process.

The principal method in general use for large-scale DNA sequencing is the chain termination method. This method was first developed by Sanger and Coulson (Sanger et al. Proc. Natl. Acad. Sci. USA 1977; 74: 5463–5467), and relies on the use of dideoxy derivatives of the four nucleoside triphosphates which are incorporated into the nascent polynucleotide chain in a polymerase reaction. Upon incorporation, the dideoxy derivatives terminate the polymerase reaction and the products are then separated by gel electrophoresis and analysed to reveal the position at which the particular dideoxy derivative was incorporated into the chain.

Although this method is widely used and produces reliable results, it is recognised that it is slow, labour-intensive and expensive.

An alternative sequencing method is proposed in EP-A-0471732, which uses spectroscopic means to detect the incorporation of a nucleotide into a nascent polynucleotide strand complementary to a target. The method relies on an immobilised complex of template and primer, which is exposed to a flow containing only one of the different nucleotides. Spectroscopic techniques are then used to measure a time-dependent signal arising from the polymerase catalysed growth of the template copy. The spectroscopic techniques described are surface plasmon resonance (SPR) spectroscopy, which measures changes in an analyte within an evanescent wave field, and fluorescence measuring techniques. However, limitations of this method are recognised; the most serious for the SPR technique being that, as the size of the copy strand grows, the absolute size of the signal also grows due to the movement of the strand out of the evanescent wave field, making it harder to detect increments. The fluorescence measuring techniques have the disadvantage of increasing background interference from the fluorophores incorporated on the growing nascent polynucleotide chain. As the chain grows, the background "noise" increases and the time required to detect each nucleotide incorporation needs to be increased. This severely restricts the use of the method for sequencing large polynucleotides.

There is therefore a need for an improved method for determining the sequence of polynucleotides which significantly increases the rate at which a polynucleotide is sequenced and which is preferably carried out by an automated process, reducing the complexity and cost associated with existing methods.

SUMMARY OF THE INVENTION

The present invention is based on the realisation that the measurement of electromagnetic or other radiation can be used to detect a conformational and/or mass change in a polymerase enzyme which occurs when a nucleotide is incorporated into a nascent polynucleotide strand.

According to the present invention, a method for sequencing a polynucleotide comprises the steps of:

(i) reacting a target polynucleotide with a polymerase enzyme immobilised on a solid support, and the different nucleotides, under conditions sufficient for the polymerase reaction; and (ii) detecting the incorporation of a specific nucleotide complementary to the target polynucleotide, by measuring radiation.

The radiation may be applied to a sample using a number of techniques, including surface-sensitive detection techniques, where a change in the optical response at a solid optical surface is used to indicate a binding interaction at the surface. In a preferred embodiment of the invention, the technique used is evanescent wave spectroscopy, in particular surface plasmon resonance (SPR) spectroscopy.

In an embodiment of the invention, the nucleotides used in the method include a blocking group at the 3' position, and optionally at the 5' position, which prevents incorporation of the nucleotides into the polynucleotide strand. However, the blocking groups may be selectively removed to allow incorporation to occur. By using the blocked nucleotides, it is possible for the method to be carried out using all the nucleotides present in the reaction at any one time. The selective removal of the blocking groups is carried out in a way that ensures the detection of each incorporated nucleotide. The method may therefore proceed on a "real-time" basis, to achieve a high rate of sequence analysis.

DESCRIPTION OF THE DRAWINGS

The invention will be described by way of example only with reference to the following drawings, where.

DESCRIPTION OF THE INVENTION

The present method for sequencing a polynucleotide involves the analysis of the kinetic interaction between a polymerase enzyme, a target polynucleotide and a complementary nucleotide. Measurement of the kinetic interaction is carried out by monitoring the changes in or absorption of electromagnetic or other radiation that occurs if the reaction proceeds.

The term "polynucleotide" as used herein is to be interpreted broadly, and includes DNA and RNA, including modified DNA and RNA, as well as other hybridising nucleic acid-like molecules, e.g. peptide nucleic acid (PNA).

Typically, the method is carried out by applying electromagnetic radiation, by using the techniques of surface plasmon resonance or nuclear magnetic resonance. However, other techniques which measure changes in radiation may be considered, for example spectroscopy by total internal reflectance fluorescence (TIRF), attenuated total reflection (ATR), frustrated total reflection (FTR), Brewster angle reflectometry, scattered total internal reflection (STIR) or evanescent wave ellipsometry.

Techniques other than those requiring electromagnetic radiation are also envisaged, in particular photochemical techniques such as chemiluminescence, and gravimetric techniques including resonant systems such as surface acoustic wave (SAW) techniques and quartz crystal microbalance (QCM) techniques.

Surface plasmon resonance (SPR) spectroscopy is a preferred method, and measures the properties of a solution by detecting the differences in refractive index between the bulk phase of the solution and the evanescent wave region. Incident monochromatic light is reflected at a specific angle off a solid optical (sensor chip) surface on the opposite side to a sample under study. The light extends into the sample for a very short distance and is affected by an interaction at the surface.

Suitable sensor chips are known in the art. Typically, they comprise an optically transparent material, e.g. glass, and a thin reflective film, e.g. silver or gold. For a review of SPR spectroscopy see European Patent Publication No. 0648328 (the entire disclosure of which is incorporated herein by reference).

Nuclear magnetic resonance (NMR) spectroscopy is another preferred method, and measures the magnetic properties of compounds. Nuclei of compounds are energetically orientated by a combination of applied magnetic field and radio-frequency radiation. When the energy exerted on a nucleus equals the energy difference between spin states (the difference between orientation parallel or anti-parallel to the direction of the applied fields), a condition known as resonance is achieved. The absorption and subsequent emission of energy associated with the change from one spin state to the other, is detected by a radio-frequency receiver.

An important aspect of the method of the present invention is the use of a polymerase enzyme immobilised onto a solid support. Immobilisation of the polymerase offers several important advantages for the success of this method. Firstly, the problem of random "noise" associated with measuring energy absorption in soluble molecules is reduced considerably. Secondly, the problem of noise from the interaction of any substrate (e.g. nucleotides) not directly involved with the polymerase is reduced, as the polymerase can be maintained within a specifically defined area relative to the field of measurement. This is particularly relevant if the technique used to measure the changes in radiation requires the measurement of fluorescence, as in TIRF, where background fluorescence increases as the nascent chain grows. Also, if SPR spectroscopy is used, the polymerase reactions are maintained within the evanescent wave field and so accurate measurements can be made irrespective of the size of the polynucleotide. Finally, as neither the target polynucleotide nor the oligonucleotide primer is irreversibly attached to the solid surface, it is relatively simple to regenerate the surface, to allow further sequencing reactions to take place using the same immobilised polymerase.

Immobilisation may be carried out using standard procedures known in the art. In particular, immobilisation using standard amine coupling procedures may be used, with attachment of ligand-associated amines to, say, a dextran or N-hydroxysuccinimide ester-activated surface. In a preferred embodiment of the invention, the polymerase is immobilised onto a SPR sensor chip surface which maintains the polymerase in close proximity to the sensor surface where changes in the refractive index may be measured. Examples of procedures used to immobilise biomolecules to optical sensors are disclosed in EP-A-0589867, and Löfas et al., Biosens. Bioelectron. (1995) 10:813–822.

The polymerase used in the invention may be of any known type. For example, the polymerase may be any DNA-dependent DNA polymerase. If the target polynucleotide is a RNA molecule, then the polymerase may be a RNA-dependent DNA polymerase, i.e. reverse transcriptase, or a RNA-dependent RNA polymerase, i.e. RNA replicase. In a preferred embodiment of the invention, the polymerase is Tag polymerase. In a further preferred embodiment of the invention, the polymerase is either E. coli polymerase III holoenzyme (McHenry, Ann. Rev. Biochem. 1988; 57:519), T7 polymerase (Schwager et al., Methods in Molecular and Cellular Biology (1989/90); Vol.1(4):155–159, or Bacteriophage T7 gene 5 polymerase complexed with E. coli Thioredoxin (Tabor et al., J. Biol. Chem. (1987); 262:1612–1623). Each of these polymerase enzymes allows a binding with the target polynucleotide to occur with high fidelity and therefore maintains a polymerase-polynucleotide complex, even when polymerisation is not actively taking place.

The polymerase III holoenzyme is composed of three subassemblies that function to create the processive enzyme: (I) the polymerase core, including the polymerase subunit α; (II) β-dimer subunit which acts as a bracelet-like structure around DNA; and (III) a subassembly of two subunits, τ and γ, used to bind and hydrolyse ATP to form the β-dimer around the DNA.

As a first step in the sequencing process, the target polynucleotide may be brought into contact with an appropriate primer in hybridising/polymerisation buffer. Typically, the buffer will be at a sufficiently high temperature to disrupt (or melt) any secondary structures that exist on the target polynucleotide. On cooling, the primer will anneal to its complement on the target. This sample may then be brought into contact with the immobilised polymerase, to form the target polynucleotide/polymerase complex.

In one embodiment of the invention, the addition of the nucleotides is controlled so that the different nucleotides are added sequentially to the polymerase/target complex. For example, dGTP may be added and allowed to flow over the polymerase/polynucleotide complex; any incorporation is then detected. Unbound dGTP flows out of the reaction site and a further nucleotide is introduced. In this manner, the detection of a kinetic interaction can be correlated to the particular nucleotide present at that time and the polynucleotide sequence can therefore be determined.

The method may also be carried out with all the different nucleotides present. For this to be carried out successfully, it is necessary for the nucleotides to incorporate a blocking group at least at the 3' position, but preferably at the 3' and 5' positions. The blocking groups may be light-sensitive and can be removed by applying light of a defined wave length, to release the active molecule. If the nucleotides incorporate blocking groups at both the 3' and 5' positions, the blocking groups should be capable of being distinguished on the basis of their spectral absorbancy, i.e. it should be possible to remove selectively one of the blocking groups by applying a specific wavelength of light which does not remove the other blocking group. It is also desirable that the blocking group at the 3' position requires the light to be applied for a longer duration than that required to remove the blocking group at the 5' position. This allows the blocking groups to be distinguished by both spectral and temporal means.

Generally, the light-sensitive blocking groups undergo photolysis at wavelengths in the range from 200 nm to 450 nm. The blocking groups will typically be derived from a compound of the formula $R^1$-[O-CO-]$^x$ wherein $R^1$ is a photolabile group and X is a leaving group. For example, $R^1$ is o-nitrobenzyl. Particularly preferred blocking groups include the o-nitrobenzyl protecting groups described in WO-A-92/10092 and WO-A-97/39151. These groups include nitroveratryloxycarbonyl (NVOC) nitropiperonyloxycarbonyl (NPOC), α-methyl-nitroveratryloxycarbonyl (MeNVOC), α-methyl-nitropiperonyloxycarbonyl (MeNPOC) and 1-pyrenylmethyloxycarbonyl (PYMOC).

A suitable 3' blocking group is a (4,5-dimethoxy-2-nitrobenzyl)oxycarbonyl group which can be formed by reaction of the nucleotide with a compound of formula (I):

wherein R is any suitable esterifying group, e.g. methyl. This blocking group can be selectively removed by a pulse of light with a wavelength of 360 nm.

A suitable blocking group at the 5' position is 1-(2-nitrophenyl)ethyl group (II):

wherein R is any suitable functional group, e.g. halogen. This blocking group may be selectively removed at a wavelength of 260 nm.

By way of example, double-blocked nucleotides are injected over the primed target polynucleotide (held in association with a high fidelity polymerase complex), and monochromatic light is focussed upstream of the polymerase at a wavelength sufficient to release the blocking group from the terminal phosphate of each nucleotide. The nucleotides are then able to flow over the bound polymerase, and incorporation into the nascent polynucleotide strand can occur. However, as the blocking group at the 3' position remains bound, only one nucleotide is incorporated. A measurement of the kinetic interaction will therefore provide information as to the particular nucleotide incorporated into the nascent chain. The polymerase used may be a high fidelity polymerase which does not dissociate readily from the target when the reaction stops. Alternatively, a competitive inhibitor may be used to prevent the polymerase dissociating from the target.

After measuring the incorporated nucleotide, a pulse of monochromatic light is focused on the blocking group within the polymerase catalytic site, to remove the blocking group at the 3' position. The monochromatic light may be pulsed for a longer duration than that required for removal at the 5' position, and so only the blocking group associated with the nucleotide in the polymerase complex will undergo removal. This reduces the likelihood of the addition of nucleotides not associated with the polymerase complex.

Once the 3' blocking group is released, the polymerase reaction is allowed to continue as further nucleotides arrive at the polymerase reaction site. Uncontrolled polymerisation is prevented by alternating the pulses of light required to remove the blocking groups.

While it is preferred to use the double-blocked nucleotides, as described above, the procedure may also be carried out using nucleotides having a blocking group at the 3' position only. In this case, it is desirable to use a competitive inhibitor of the polymerase, which will reduce the probability of a nucleotide lacking a blocking group at the 3' position being incorporated into the nascent chain. A suitable competitive inhibitor of polymerase is carbonyldiphosphonate (COMDP).

The following Example illustrates the invention with reference to the drawings.

EXAMPLE

The following analysis was carried out on a modified BIAcore 2000 system (BIAcore AB, UPPSALA, Sweden) with a sensor chip CM5 (Research grade, BIAcore AB) as the optical sensor surface. The instrument was provided with an integrated μm-fluidic cartridge (IFC) which allows analysis in four cells by a single sample injection.

Preparation of Polymerase

E. Coli polymerase III holoenzyme was prepared according to (Millard et al., Methods Enzymol. (1995); 262:22) using hydrophobic interaction chromatography on valyl-Sepharose, to purify the holoenzyme at high salt concentrations. After purification, the hollow enzyme was concentrated using the ion-filtration technique described by Kirkegaard et al, Anal. Biochem. (1972); 50:122.

Immobilisation of the Polymerase

Immobilisation of the polymerase to the sensor chip surface was carried out according to (Jönsson et al., Biotechniques (1991); 11:620–627). Briefly, the sensor chip environment was equilibrated with Hepes buffer (10 mM Hepes, 150 mM NaCl, 0.05% surfactant P20(BIAcore AB, Uppsala, Sweden), pH 7.4). Equal volumes of N-hydroxysuccinimide (0.1 M in water) and N-ethyl-n'-(dimethylaminopropyl) carbodiimide (EDC) (0.1 M in water) were mixed together and injected across the chip (CM5) surface, to activate the carboxymethylated dextran. The polymerase III Subassembly core (160 μl, 500 U) was mixed with 10 mM sodium acetate (100 μl, pH 5) and injected across the activated surface. Finally, residual N-hydroxysuccinimide esters on the sensor chip surface were reacted with ethanolamine (35 μl, 1 M in water, pH 8.5), and non-bound polymerase was washed from the surface. The immobilisation procedure was performed with a continuous flow of Hepes buffer (5 μl/min) at a temperature of 25° C.

Oligonucleotides

Two oligonucleotides were synthesised using standard phosphoramidite chemistry. The oligonucleotide defined as SEQ ID No. 1 was used as the target polynucleotide, and the oligonucleotide defined as SEQ ID No. 2 was used as the primer.

CAAGGAGAGGACGCTGTCTGTCGAAGGTAAGGAACGGACGAGAGAAGGGAGAG  SEQ ID No. 1

CTCTCCCTTCTCTCGTC  SEQ ID No. 2

The two oligonucleotides were reacted under hybridising conditions to form the target-primer complex.

The primed DNA was then suspended in buffer (20 mM Tris-HCl, pH 7.5, 8 mM $MgCl_2$, 4% (v/v) glycerol, 5 mM dithiothreitol (DDT), 40 μg bovine serum albumin) containing 21 μg ssDNA binding-protein and the DNA pol III sub-assembly, required to form the bracelet-like structure (1.6 pmol β-dimer and 195 fmol γ subunits). 0.5 mM ATP was present together with 60 μM carbonyldiphosphonate (COMDP). In this reaction, the γ subunit acts as a molecular matchmaker, hydrolysing ATP to place the β-dimer subunits onto the DNA to form the polymerase sub-assembly (Studwell et al, UCLA Symp. Mol. Cell. Biol. New Ser. 1990; 127: 153).

The primed DNA/sub-assembly complex was then injected over the polymerase III on the sensor chip surface at a flow-rate of 5 μm/min, and allowed to bind to the polymerase via the action of the γ subunits.

In this experiment, magnesium and ATP are needed for the Pol III to bind to the primed DNA. However, magnesium also promotes removal of the primer by the proof-reading 3'→5' exonuclease activity. This problem is circumvented by including the carbonyldiphosphonate, which is a competitive inhibitor of polymerase activity (a pol III lacking the 3'→5 exonuclease activity may be used to avoid this particular problem).

A continuous flow of 60 μM carbonyldiphosphonate was maintained over the chip surface, to prevent the exonuclease activity from removing the primer from the target DNA.

Nucleotides Incorporating Two Blocking Groups

Figure 3:
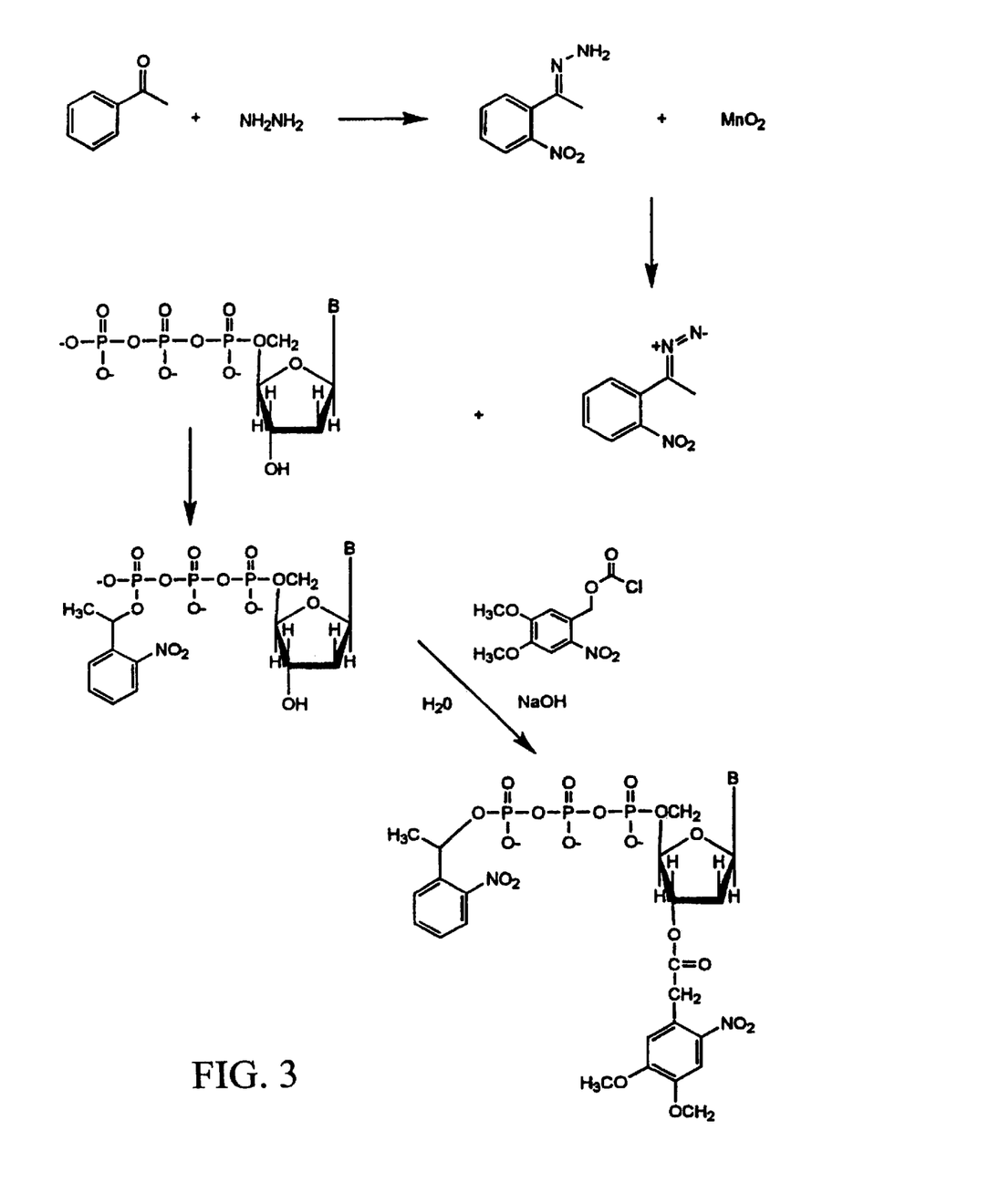
FIG. 3 illustrates the synthesis procedure for the double blocked nucleotides.

Each nucleotide (dCTP, dTTP, dGTP and dATP) contained a 1-(2-nitrophenyl)ethyl blocking group at the 5' position, and a (4,5-dimethoxy-2-nitrobenzyl) oxycarbonyl blocking group at the 3' position as shown in FIG. 3. The synthesis of the double blocked nucleotides was as follows:

Stage 1:- synthesis of (4,5-dimethozy-nitrobenzyl) oxycarbonyl-nucleoside triphosphate.

The same overall method was applied to dGTP, dCTP and dTTP. A mixture of dATP dihydrate (0.4 mmol) and approximately 3 mmol of 4,5-dimethoxy-2-nitrophenyldiazomethane, freshly prepared from 900 mg (4 mmol) of 4,5-dimethoxy-2-nitrophenylhydrazone (synthesized by treatment of 6-nitroveraldehyde with hydrazine monohydrate in chloroform by the procedure of Wootton and Trentham, Photochemical Probes in Biochemistry (Nielsen, P. E., Ed,) NATO ASI Ser. C, Vol. 272, p277–296 (1989), was stirred in 15 ml of DMSO at room temperature in the dark for 40 h. Monitoring of the reaction by TLC in a chloroform/methanol (5:1 v/v) solvent system revealed the appearance of a spot with Rf 0.54 corresponding to the caged nucleotide. DMSO, unreacted diazo compound, and reaction products with low polarity were removed by repetitive extraction with 60 ml of ether. The residual material, which, among other substances, contained unreacted nucleotide and the desired product, was dissolved in a minimal amount of chloroform and separated by flash chromatography on a silica column (3×30 cm). Elution using 100% chloroform and methanol/chloroform (95:5 v/v) removed the hydrophobic side products of 4,5-dimethoxy-2-nitrophenyldiazomethane from the column. The fractions were dried on a rotary evaporator. 78 mg of the caged product was then lyophilised. The overall yield was 45%. The 3' blocked 4,5-dimethyloxy-2-nitrobenzyl oxycarbonyl dATP was isolated directly with higher purity by preparative reverse-phased HPLC from the crude product.

Stage 2:- Addition of the 5' 1-(2-nitrophenyl)ethyl group to the 3' 4,5-dimethoxy-2-nitrobenzyl oxycarbonyl blocked dATP .

A mixture of 4,5-dimethoxy-2-nitrobenzyl oxycarbonyl 5' dATP (0.4 mmol) and approximately 3 mmol of 1-(2-nitrophenyl)diazoethane, freshly prepared from 716.7 mg (4 mmol) of hydrazone of 2-nitroacetophenone (synthesized by treatment of 2-nitroacetophenone with hydrazine monohydrate in ethanol) and 2.9 g (30 mmol) of $MnO_2$ (90%) in 20 ml of chloroform by the procedure of walker et al (walker et al, Methods Enzymol. 1989; 172:288–301), was stirred in 15 ml of DMSO at room temperature in the dark for 40 h. Monitoring the reaction by TLC in a chloroform/methanol (5:1 v/v) solvent system revealed the appearance of a pair of spots with Rf 0.68 and Rf 0.58, corresponding to the two diasterioisomers of the axial and the two diasteroisomers of the equatorial form of the 1(2-nitrophenyl)ethyl ester of 4,5-dimethoxy-2-nitrobenzyl oxycarbonyl 5' dATP, respectively. DMSO, unreacted diazo compound, and reaction products with low polarity were removed by repetitive extraction with 50 ml ether.

The residual material, which contained among other substances unreacted 4,5-dimethoxy-2-nitrobenzyl oxycarbonyl 5' dATP and the desired double blocked dATP, was dissolved in a minimal amount of chloroform and separated by flash chromatography on a silica column 3×30 cm. Elution using 100% chloroform removed hydrophobic side products of 1-(2-nitrophenyl)diazoethane from the column. The product was dried on a rotary evaporator. Lyophilization gave 74 mg of the caged compound. The overall yield was 57%. 0.2 mM of each nucleotide was present in the polymerisation buffer (1 mM Tris-HCl pH 8.8, 5 mM KCl, 0.15 mM $MgCl_2$, 0.01% (w/v) gelatin).

DNA Sequencing

Figure 1:
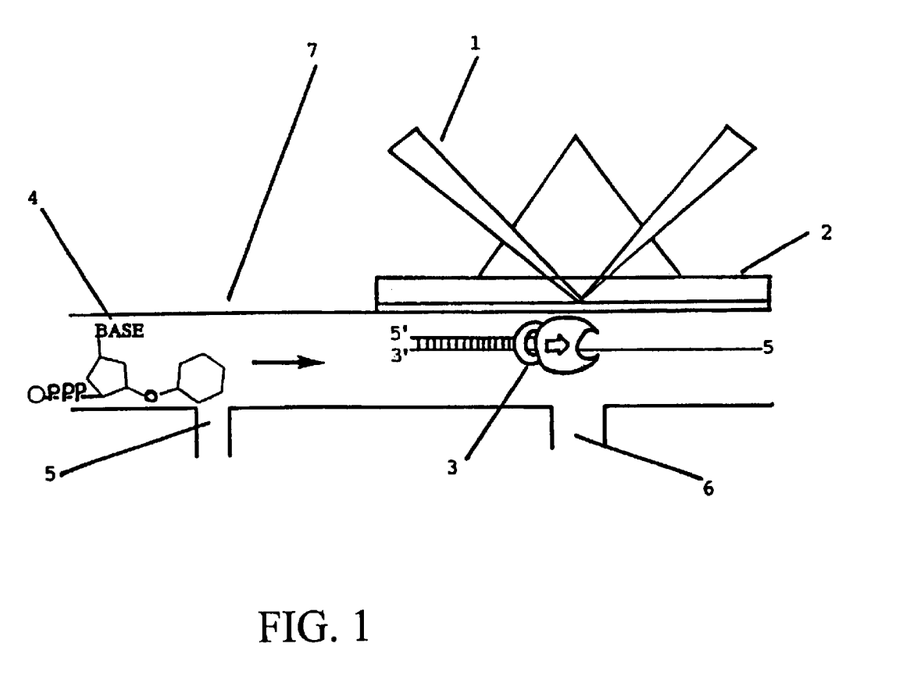
FIG. 1 is a schematic illustration of polynucleotide sequence analysis using SPR spectroscopy.

FIG. 1 shows a SPR sensing system and fluidic cell (7), having a means for applying electromagnetic radiation (1) to a sensor chip (2) with an immobilised polymerase enzyme (3) at the sensor surface, an inlet (4) for introducing the different nucleotides into the cell and two focusing assemblies (5) and (6) for pulsing monochromatic light into the cell.

The different nucleotides are introduced into the fluidic cell (7) at a flow rate of 30 μl/min., at a temperature of 25° C. and a data collection rate of 10 Hz. As the nucleotides pass the focusing assembly (5), monochromatic light at a wavelength of 260 nm is pulsed to remove the blocking group at the 5' position. The nucleotides then flow over the sensor chip (2) and contact the target polynucleotide/polymerase complex (3) which is held in place by the β-dimer sub-assembly. Since the 3' position on the primer sequence is free to react, polymerisation may take place as a nucleotide is incorporated onto its complement on the target polynucleotide. This incorporation is then detected by the monochromatic p-polarised light of the SPR device. No further polymerisation occurs, since the incorporated nucleotide has a blocking group at the 3' position. Monochromatic light of wavelength 360 nm is then pulsed by the focusing assembly (6) at the site of polymerisation. The high flow rate in the fluidic cell ensures that nucleotides not bound to the polymerase are removed from the cell before sufficient energy has been absorbed to release their 3' blocking groups.

Once the 3' blocking group has been released from the polymerised nucleotide, further polymerisation may occur.

Figure 2A:
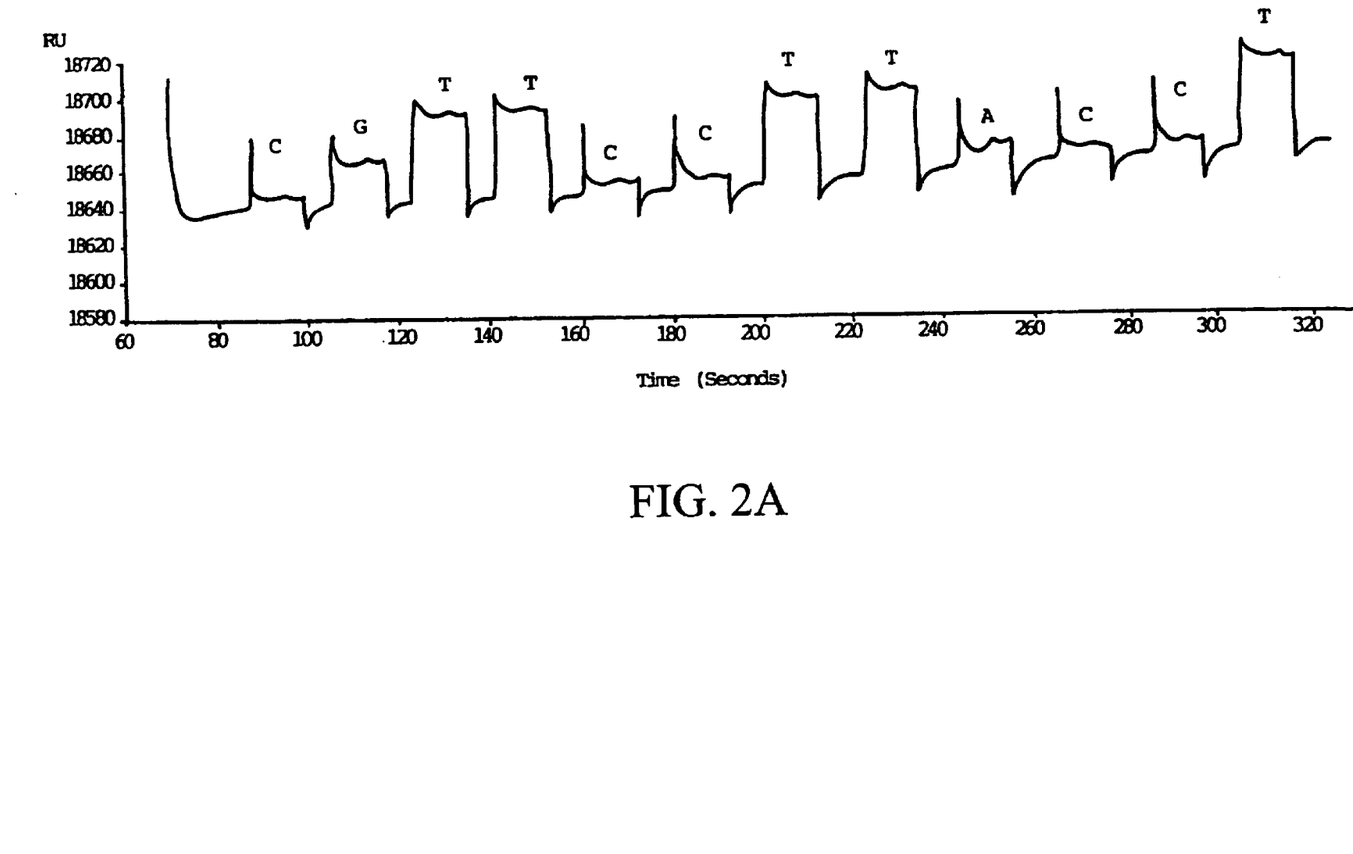
FIG. 2 illustrates the different response signals detected for the polymerisation of each of the different nucleotides.
Figure 2B:
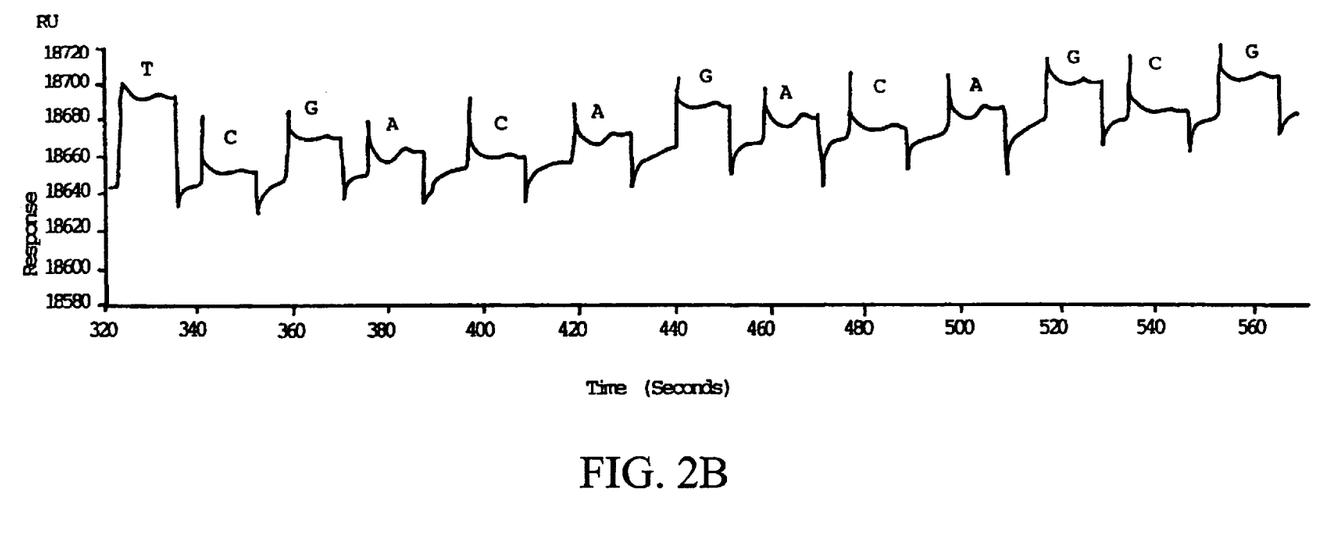
Figure 2C:
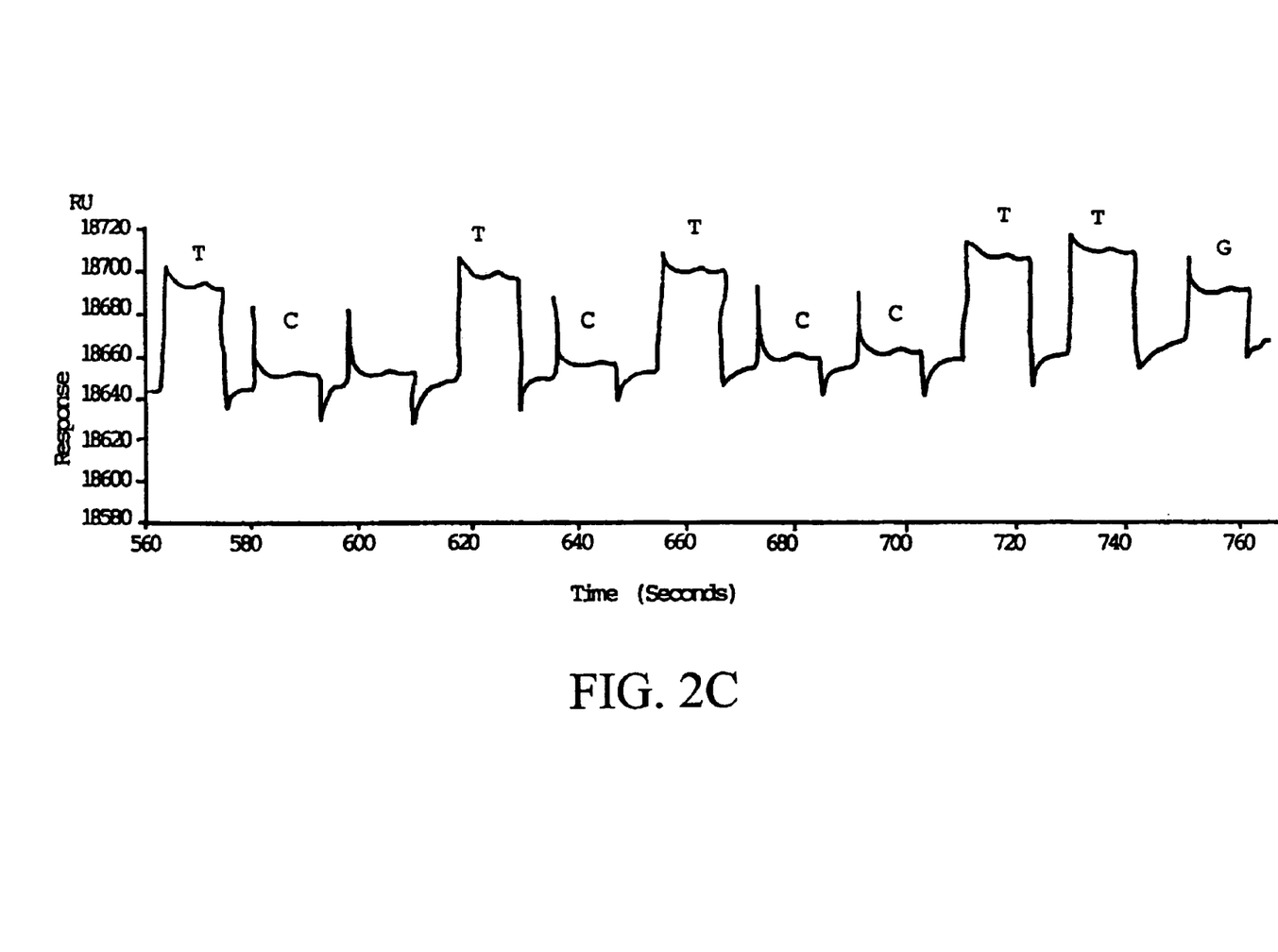

FIG. 2 shows the results from the sequencing experiment with each nucleotide incorporated into the nascent chain being detected. The results show a sequence complementary to that of SEQ ID No. 1.

6. The method according to claim 5, wherein the nucleotides comprise a further blocking group at the terminal phosphate group of the triphosphate chain, and the further blocking group is removed prior to the removal of the 3' blocking group.

7. The method according to claim 6, wherein the further blocking group can be selectively removed by pulsed monochromatic light under conditions different from those required to remove the 3' blocking group.

8. The method according to claim 7, wherein the further blocking group is removed by pulsing the monochromatic light for a duration different from that required to remove the 3' blocking group.

What is claimed is:

1. A method for sequencing a polynucleotide, comprising the steps of:
   (i) reacting a target polynucleotide with a polymerase, wherein said polymerase is immobilised on a solid support, and nucleotides, under conditions sufficient for the polymerase reaction; and
   (ii) detecting the interaction between the polymerase, the target polynucleotide and each specific nucleotide complementary to the target polynucleotide, that is incorporated into a nascent polynucleotide being synthesized as a result of the polymerase reaction, to thereby determine the sequence of the target polynucleotide, the detection being carried out by using surface plasmon resonance to measure a change in, or absorption of, radiation that occurs during the interaction.

2. The method according to claim 1, wherein steps (i) and (ii) are conducted with each of the complementary nucleotides in turn, until incorporation is detected, and then repeated.

3. The method according to claim 1, wherein step (i) is conducted with all the complementary nucleotides present.

4. The method according to claim 1, wherein the nucleotides comprise a 3' blocking group which is removed after the polymerase reaction.

5. The method according to claim 4, wherein the blocking group is selectively removed by pulsed monochromatic light.

9. The method according to claim 4, wherein the nucleotides comprise a further blocking group at the terminal phosphate group of the triphosphate chain, and the further blocking group is removed prior to the removal of the 3' blocking group.

10. The method according to claim 9, wherein the further blocking group is selectively removed by pulsed monochromatic light under conditions different from those required to remove the 3' blocking group.

11. The method according to claim 10, wherein the further blocking group is removed by pulsing the monochromatic light for a duration different from that required to remove the 3' blocking group.

12. The method according to claim 1, wherein step (i) further comprises introducing a competitive inhibitor of the polymerase.

13. The method according to claim 1, wherein the target polynucleotide of step (i) is bound to the polymerase by a $\beta_2$ dimer complex.

14. The method according to claim 1, wherein the polymerase is *E. coli* DNA polymerase III or T7 polymerase.

15. The method according to claim 1, wherein the polymerase is Taq polymerase.

16. The method according to claim 1, wherein the polymerase is reverse transcriptase.

17. The method according to claim 1, wherein step (ii) comprises detection of a change in resonance signal over time.

18. The method according to claim 1, wherein the radiation is electromagnetic.

19. The method according to claim 18, wherein the electromagnetic radiation is in the infra-red spectrum.

20. The method according to claim 1, wherein the polynucleotide is DNA.

21. The method according to claim 1, wherein steps (i) and (ii) are conducted with each of the complementary nucleotides in turn, until incorporation is detected, and then repeated.

22. The method according to claim 1, wherein step (i) is conducted with all the complementary nucleotides present.

23. The method according to claim 1, wherein the nucleotides are not labeled.

24. The method according to claim 1, wherein the effect detected results from a conformation or mass change of the polymerase that occurs upon incorporation of the nucleotide.

* * * * *

UNITED STATES PATENT AND TRADEMARK OFFICE
CERTIFICATE OF CORRECTION

| | | |
|---|---|---|
| PATENT NO. | : 7,008,766 B1 | Page 1 of 1 |
| APPLICATION NO. | : 09/463549 | |
| DATED | : March 7, 2006 | |
| INVENTOR(S) | : Daniel Henry Densham | |

It is certified that error appears in the above-identified patent and that said Letters Patent is hereby corrected as shown below:

<u>Column 10,</u>
Line 1, "The method according to claim 5" should read -- The method according to claim 4 --.

Line 41, "The method according to claim 4" should read -- The method according to claim 5 --.

Lines 46 and 47, "the further blocking group is selectively removed" should read -- the further blocking group can be selectively removed --

Signed and Sealed this

Twentieth Day of March, 2007

JON W. DUDAS
*Director of the United States Patent and Trademark Office*

SEQUENCE LISTING

```
<160> NUMBER OF SEQ ID NOS: 2

<210> SEQ ID NO 1
<211> LENGTH: 53
<212> TYPE: Nucleic acid
<213> ORGANISM: Artificial sequence
<220> FEATURE:
<223> OTHER INFORMATION: Synthetic oligonucleotide used as target
      polynucleotide

<400> SEQUENCE: 1
caaggagagg acgctgtctg tcgaaggtaa ggaacggacg agagaaggga gag           53

<210> SEQ ID NO 2
<211> LENGTH: 17
<212> TPYE: Nucleic acid
<213> ORGANISM: Artificial sequence
<220> FEATURE:
<223> OTHER INFORMATION: Synthetic oligonucleotide used as primer

<400> SEQUENCE: 2
ctctcccttc tctcgtc                                                  17
```